United States Patent [19]

Åberg et al.

[11] 4,081,316
[45] Mar. 28, 1978

[54] METHOD FOR PRODUCING FLUFFED PULP

[75] Inventors: Sven Ulrik Torbjörn Åberg; Sven Gunnar Bergdahl, both of Molnlycke, Sweden

[73] Assignee: Molnlycke AB, Goteborg, Sweden

[21] Appl. No.: 636,702

[22] Filed: Dec. 1, 1975

[30] Foreign Application Priority Data

Dec. 5, 1974 Sweden .............................. 7415256

[51] Int. Cl.$^2$ .................. D21B 1/02; D21B 1/32; D21D 1/02; D21F 11/14

[52] U.S. Cl. .......................................... 162/4; 162/28; 162/100; 162/142; 162/147; 241/28

[58] Field of Search .................. 162/1, 4, 5, 6, 23, 162/28, 100, 142, 147; 34/10; 241/17, 18, 28; 128/290 R, 290 P, 296; 264/121

[56] References Cited

U.S. PATENT DOCUMENTS

| | | | |
|---|---|---|---|
| 3,377,234 | 4/1968 | Illingworth | 162/5 |
| 3,446,696 | 5/1969 | Illingworth | 162/5 |
| 3,454,463 | 7/1969 | Welsh | 162/142 |
| 3,627,630 | 12/1971 | Gagnon | 162/100 |

*Primary Examiner*—Richard V. Fisher
*Attorney, Agent, or Firm*—Young & Thompson

[57] ABSTRACT

Improved fluffed pulp consisting of 95 to 25 percent by weight groundwood and 5 to 75 percent by weight chemical pulp, with a liquid retention capacity of at least 6.5 gram liquid per gram pulp, a liquid dispersing capacity of at least 2.5 gram liquid per gram pulp per minute, a bulk of at least 18 cm$^3$/gram and a web strength of at least 0.2 Newton, and a method of producing said pulp by mixing 95 to 25 percent by weight groundwood and 5 to 75 percent by weight chemical pulp beaten in a wet state with each other, dewatering mechanically to a dry solids content of 40 to 50 percent by weight, coarse-defibrating, drying in a flash drying step to 60 to 85 percent by weight, finish-defibrating and finish-drying to 80 to 95 percent by weight dry solids content.

4 Claims, No Drawings

METHOD FOR PRODUCING FLUFFED PULP

The present invention relates to a method of producing fluffed pulp, and a fluffed pulp from which fibre webs or batts can be made which have higher strength and absorption than has been possible with presently employed dry defibrated cellulose pulps.

Such fibre batts are used for producing absorption bodies in a number of disposable products such as diapers, sanitary napkins, hospital products, etc.

Several processes are already known for the dry production of a fibre batt of cellulose pulp. The cellulose, broken down into separate fibres, is usually mixed with a stream of air into a fibre suspension which is blown against a fine mesh Fourdrinier wire. The air passes through the wire while the cellulose fibres are retained to form a fibre layer. In the continuous production of a fibre batt, the wire is kept moving continuously, e.g. at right angles to the air stream, so that the fibre batt is built up to desired thickness during the passage of the wire through the air stream. To obtain a fibre batt with as even basis weight as possible, the fibre suspension should have little variation in concentration. This is usually achieved by having the initial pulp, in the form of a web, taken at constant speed into a defibrating apparatus through which the air stream also passes. When the same amount of pulp per unit time is thus continuously supplied to the air stream, the variations of the fibre concentration with time will be very small.

In order that the fibre batt formed shall have the greatest possible strength, the amount of remaining undefibrated portions of the initial pulp should be small, and furthermore, the fibres forming the batt should have the greatest possible length. Defibration shall thus be as complete as possible, while avoiding rupture of the fibres in the initial pulp. To facilitate gentle defibration, the initial pulp can be pretreated. A common method is to weaken the fibre bonds in the initial pulp by special processes in its production, e.g. light pressing in the wet machine and/or treatment with chemical preparations. Such pulp with weakened fibre bonds, intended for dry defibration, is manufactured and sold commercially under the designation "fluffed pulp". The majority of all fluffed pulp is manufactured and sold in the form of webs reeled up into rolls, and only a minor portion is produced in the form of sheets, stacked and compressed into bales.

Fluffed pulp is more expensive to produce than ordinary paper pulp. Loose pressing in the wet machine involves reduction of the amount of water which is mechanically pressed out of the pulp. A correspondingly large amount of heat is therefore consumed for drying. Treatment with chemical preparations involves material costs for the preparations and handling costs in the process.

It is also more expensive to produce pulp in the form of rolls than in the form of bales. Roll manufacture involves extra machinery and staff, and the cost of wrapping and transporting roll pulp is higher than the corresponding costs for bale pulp. In summary, fluffed pulp in rolls is 10-20% more expensive than paper pulp in bales, and fluffed pulp in bales is 5-15% more expensive than paper pulp in bales.

To separate the individual fibres from each other, the pulp can be dry-defibrated by several different methods: with hammer mills, toothed shreaders, or disc refiners. These defibrating arrangements function satisfactorily only with pulp in which the individual fibres are bonded by relatively weak forces, as otherwise the amount of undefibrated bunches of fibres obtained is too great. One is therefore reduced to using the more expensive fluffed pulp for dry-defibration.

A method of dry-defibration which, under suitable conditions, can give acceptable defibration of pulps, even where the fibre bondings are not exceptionally weak, is defibration in so-called disc refiners. In certain cases, even ordinary conventional pulp can be dry-defibrated satisfactorily in disc refiners.

To circumvent the difficulties in dry-defibration, it has been proposed to defibrate the pulp before it is finish-dried. The strong bonds between the fibres are first established when the water has been almost entirely expelled from the pulp. According to U.S. application Ser. No. 211,256, filed Dec. 23, 1971, now abandoned, which corresponds to British Pat. No. 1,367,670, pulp with a moisture content of 25-60% is defibrated, whereafter it is dried in a so-called "flash drier" and transferred by a stream of air to a receiving apparatus for forming a fibre batt. It is claimed that conventional paper pulp can be defibrated in this way so that only a very small amount of undefibrated fibre bunches remains.

It is thus characteristic of all previously used processes for the production of defibrated pulp that one starts with a pulp in which the fibre bonding forces are in all cases no greater than in conventional paper pulp. The pulp is then defibrated in the gentlest possible way in order to separate the fibres without subsequent shortening of fibres, dust formation or other damage to the fibres.

According to the present invention, defibrated pulp is produced from a cellulose material which has intentionally been treated so that substantially higher bonding forces are formed between the separate fibres than is the case with conventional paper pulp, and so that the fibres are hereby intentionally exposed to damage for obtaining breakages and for damaging the fibre surface. The intention is to provide in such a way a pulp which is better suited for use as absorption bodies, because of higher moisture absorption, better moisture spreading, increased tendency to mat together into a strong fibre batt, and increased capacity for retaining short pulp fibres of the mechanical pulp type in the fibre network.

The pulp according to the present invention is for use in products for absorbing liquids such as sanitary products, and is characterized in that it consists of 95-25% by weight mechanical wood pulp and 5-75% by weight chemical pulp, with a liquid retention capacity of at least 6.5 g liquid per gram pulp, a liquid dispersion capacity of at least 2.5 g liquid per gram pulp per minute, a bulk of at least 18 $cm^3$ per gram and a web strength of at least 0.2 Newton. More than 25% of the incorporated pulp, that is, the total pulp, consists of waste fibers that have been obtained by deinking paper scrap. The method for producing such pulp is characterized in that 95-25% by weight mechanical wood pulp and 5-75% by weight chemical pulp beaten in a wet state are mixed with each other, dewatered mechanically to a dry solids content of 40-50% by weight, coarse-defibrated, dried in a flash drying step to 60-80% by weight, finish-defibrated and finish-dried to 80-95% by weight dry solids content. The coarse-defibration and finish-defibration referred to above, are merely first and second comminution steps, it being of course obvious that in the first step the starting material and the product will be coarser than will be the starting material and product of the second step. Again, the incorporated or total pulp consists of more than 25% by weight of waste fibers which have been produced by deinking paper scrap, and the chemical pulp is treated, that is beaten, before the recited drying steps so that its drainage resistance exceeds 20° SR.

In a further development of the method according to the invention, already milled paper pulp, so-called waste fibre, is incorporated in the initial pulp produced by de-inking and possibly bleaching paper scrap. The special beating step can thereby be reduced, or even eliminated altogether.

Within the paper industry, beating the pulp fibres suspended in the water to increase the strength of the paper web obtained prior to forming sheets is previously known and applied. Beating takes place in special commercially available apparatuses. During beating rupture, inter alia, of the pulp fibre skin is achieved so that the fibre surfaces takes on a brush-like or hairy appearance, and rupture points are formed on the fibres. Beaten pulp fibres mat together better for this reason, amongst others, so that paper sheets having greater strength are formed.

At the same time as the pulp is beaten, its tendency to resist water which drains through a pulp layer increases. This tendency is usually measured in a special apparatus, a drainage resistance meter, and the drainage resistance is a generally accepted quality determination for the pulp. The drainage resistance is usually expressed in Schopper-Riegler, shortened to °SR.

Commercial chemical cellulose pulps have a low drainage resistance. Some typical examples are:

| | |
|---|---|
| bleached sulphate from pine | approx. 15° SR |
| bleached sulphate from birch | approx. 14° SR |
| bleached sulphite from fir | approx. 14° SR |

A fibre web which is dry-produced from fibres from such a pulp has relatively low strength even at best, i.e. when the dry-defibration has taken place completely and without shortening of fibres. The ability of the fibre web to incorporate and retain short fibres in the network is small. The absorption capacity of the fibre web, especially if the web contains more than 25% by weight of mechanical fibre, is comparatively low.

A fibre web which is dry-produced from fibres from a pulp having a drainage resistance higher than 20° SR has, on the other hand, vastly superior strength and considerable elasticity. By reason thereof crack formation is avoided in the fibre web when it is used, and in addition the improved fibre contact and the enlarged surface of the fibres result in improved moisture absorption and a high capacity for incorporating and retaining mechanical pulp fibres in the network.

The invention will now be elucidated below by a number of working examples, showing comparisons between fluffed pulp according to the invention, ordinary fluffed pulp and ordinary pulp.

EXAMPLE 1

Rolled fluffed pulp, produced from European pine and fir according to the sulphate process, with a refining degree R 18 of 86.1, a brightness of 88% SCAN, a drainage resistance of 15° SR measured according to SCAN C 19:65, and a dry substance content of 92.4%, was treated in the following way:

The pulp was manually broken up into lumps of about 2.5 cm, which were mixed into water at room temperature. The amount of water was adjusted so that the pulp concentration was about 2%. Stirring was continued until the pulp was completely slurried in the water.

Laboratory-size sheets were made from the pulp, with a basis weight of about 500 g dry pulp per m$^2$, which were pressed between filter papers to a dry solids content of about 40%.

A portion of the pulp was dried in the form of sheets at a temperature of 110° C to about 90% dry solids content. Another portion of the pulp was disintegrated in a household mixer to fibre aggregates of 1 to about 10 fibres per aggregate. The disintegrated pulp was dried in hot air at about 290° C to about 90% dry solids content, so-called "flash drying". The dried pulp samples were fed in small portions into a Wennberg laboratory disintegrator. After disintegration, the proportion of undefibrated material, defined as pulp particles which do not pass a net with 12 meshes per inch, was 6% for both samples.

Sample bodies were made from the disintegrated pulps by feeding the pulp into an airstream which led into a cylindrical glass container the bottom of which consisted of a fine mesh net. The base area of the sample body was 50 cm$^2$ and its height was 15 cm.

The glass container was weighed to determine the bulk of the pulp. The pulp was then loaded with a pressure of 50 g/cm$^2$, whereafter the container was placed in a bath containing water at room temperature to a level of 2 cm above the bottom surface. The time for completely wetting the sample body was determined. After the container had been lifted up and extraneous water wiped away, it was reweighed for determining the liquid retention capacity of the pulp.

| Results: | Sheet-dried pulp | Flash-dried pulp |
|---|---|---|
| Bulk cm$^3$/g | 19.3 | 19.6 |
| Saturation time, minutes | 2.0 | 2.0 |
| Liquid retention capacity, g water/g pulp | 6.6 | 6.6 |

The liquid diffusion capacity, defined as absorption per pulp quantity per time unit, was calculated as:

$$\text{Sheet-dried pulp, } \frac{6.6}{2.0} = 3.30 \text{ g water/g pulp, minute}$$

$$\text{Flash-dried pulp, } \frac{6.6}{2.0} = 3.30 \text{ g water/g pulp, minute}$$

A fibre web was made from the same initial pulp by feeding 6.75 g pulp into an airstream which was allowed to pass a fine mesh net. The base area of the web was 15 × 15 cm. The bursting strength of the web was determined by allowing a dynamometer-suspended rupturing body to pass through the web.

The bursting strength of the sheet-dried pulp was 0.2 Newton.

The bursting strength of the flash-dried pulp was 0.24 Newton.

EXAMPLE 2

Rolled pulp of the same kind as in Example 1 was slurried in water in the same way. The pulp was beaten in a laboratory hollander to a drainage resistance of 20° SR.

The pulp was dried, partly in the form of sheets and partly according to the flash method, and was dry-disintegrated, sample bodies being produced and tested as in Example 1.

| Results: | Sheet-dried pulp | Flash-dried pulp |
|---|---|---|
| Proportion of non-defibrate % | 7 | 6 |
| Bulk, cm³/g | 22.6 | 23.0 |
| Time for complete wetting, minutes | 1.4 | 1.4 |
| Liquid retention capacity, grams water/grams pulp | 7.2 | 7.1 |
| Liquid spreading capacity, grams water/grams pulp × minutes | 5.15 | 5.06 |
| Bursting strength, Newton | 0.44 | 0.51 |

EXAMPLE 3

Paper pulp produced from European pine according to the sulphate process with a refining degree R 18 of 84.6, a brightness of 90% SCAN, a drainage resistance of 15° SR measured according to SCAN C 19:65 and with a dry solids content of 88.1% was slurried in water as in Example 1.

The pulp was dried in the form of sheets and according to the flash method, and was dry-disintegrated.

Sample bodies were produced and tested as in Example 1.

The experiment was repeated with pulp which had been beaten to 20° SR.

| Results: | Sheet-dried pulp unbeaten | Sheet-dried pulp 20° SR | Flash-dried pulp unbeaten | Flash-dried pulp 20° SR |
|---|---|---|---|---|
| Proportion of non-defibrate % | 8 | 7 | 7 | 8 |
| Bulk, cm³/g | 19.2 | 22.2 | 19.4 | 22.6 |
| Time for complete wetting, minutes | 1.8 | 1.0 | 1.7 | 1.1 |
| Liquid retention capacity, grams water/grams pulp | 6.5 | 7.4 | 6.6 | 7.5 |
| Liquid spreading capacity, grams water/grams pulp × minutes | 3.61 | 7.40 | 3.88 | 6.81 |
| Bursting strength, Newton | 0.20 | 0.42 | 0.21 | 0.46 |

EXAMPLE 4

Unbleached mechanical wood pulp, flash-dried to 88.2% dry solids content, with a Canadian standard freeness of 92 and brightness of 58.5% SCAN was manually broken up into about 2.5 cm lumps which were mixed with similarly broken up rolled pulp according to Example 1 and were stirred into water at room temperature. The amount of water and the dissolution time was adjusted as in Example 1.

Three different pulp mixtures were made, with 25, 60 and 95% mechanical wood pulp.

The pulps were dried according to the flash method and dry-disintegrated. Sample bodies were made and tested as in Example 1.

| Results: | 25% mechanical wood pulp | 60% mechanical wood pulp | 95% mechanical wood pulp |
|---|---|---|---|
| Proportion of non-defibrate % | 7 | 6 | 6 |
| Bulk, cm³/g | 17.2 | 16.2 | 15.5 |
| Time for complete wetting minutes | 2.6 | 2.8 | 3.1 |
| Liquid retention capacity, grams water/grams pulp | 6.4 | 6.2 | 6.0 |
| Liquid spreading capacity, grams wate/grams pulp × minutes | 2.46 | 2.14 | 1.94 |
| Bursting strength, Newton | 0.19 | 0.17 | 0.14 |

To determine the capacity of the fibre batt for incorporating and retaining mechanical pulp fibres, the procedure was as follows: A sample body of the type used in measuring bursting strength was laid on top of a wire net with 16 meshes per inch. A sheet of plexiglass was laid on top of the sample body, whereafter the net, sample body and sheet were laid on a grating with wide interspaces so that the underside of the net was practically open downwards. The plexiglass sheet was impact-loaded by having a 500 gram weight fall freely from 10 cm height against the sheet 100 times during about 5 minutes. A number of fibres were hereby liberated from the sample body and pushed through the net down onto a collecting plate. From their colour and appearance it could be determined that the ejected fibres were chiefly from mechanical pulp wood fibres.

The loss in weight of the sample body as a result of impact loading was calculated to be:
  6% for 25% mechanical wood pulp
  14% for 60% mechanical wood pulp
  22% for 90% mechanical wood pulp

EXAMPLE 5

Example 4 was repeated with the difference that the rolled pulp was beaten in a laboratory hollander to 21° SR before mixing with the mechanical wood pulp.

| Results: | 25% mechanical wood pulp | 60% mechanical wood pulp | 95% mechanical wood pulp |
|---|---|---|---|
| Proportion of non-defibrate % | 7 | 7 | 6 |
| Bulk, cm³/g | 22.2 | 19.5 | 18.0 |
| Time for complete wetting, minutes | 1.7 | 2.1 | 2.6 |
| Liquid retention capacity, grams water/grams pulp | 7.1 | 6.9 | 6.3 |
| Liquid spreading capacity, grams water/grams pulp × minutes | 4.18 | 3.29 | 2.50 |
| Bursting strength, Newton | 0.42 | 0.33 | 0.22 |
| Impact loss % | 4 | 10 | 14 |

EXAMPLE 6

Example 4 was repeated with the difference that instead of rolled pulp, paper pulp according to Example 3 was used, and before mixing with mechanical wood pulp it was beaten in a laboratory hollander to 22° SR.

| Results: | 25% mechanical wood pulp | 60% mechanical wood pulp | 95% mechanical wood pulp |
|---|---|---|---|
| Proportion of non-defibrate % | 8 | 7 | 7 |
| Time for complete wetting, minutes | 1.4 | 1.9 | 2.0 |
| Liquid retention capacity, grams water/grams pulp | 7.2 | 6.8 | 6.5 |
| Liquid spreading capacity, grams water/grams pulp × minutes | 5.14 | 3.58 | 3.25 |
| Bursting strength, Newton | 0.43 | 0.33 | 0.23 |

-continued

| Results: | 25% mechanical wood pulp | 60% mechanical wood pulp | 95% mechanical wood pulp |
|---|---|---|---|
| Impact loss % | 4 | 9 | 15 |

EXAMPLE 7

Used paper, mainly wood-free, was slurried in water at about 60° C, containing sodium hydroxide in an amount of 5% based on the weight of the paper. When the paper was thought to be well slurried, 4% soft soap was added (based on the weight of the paper) whereupon the slurry was allowed to stand under slow stirring for 90 minutes. Thereafter the slurry was transferred to another vessel through the bottom of which small air bubbles could be introduced. The pulp concentration in the mixture was about 0.7%. On blowing in air, a heavy foam was quickly formed in which washed-out printing ink from the waste paper was concentrated. The foam was removed continuously. Blowing-in of air was discontinued after 45 minutes.

A flash-dried sample of the pulp was analyzed and was found to consist mainly of pine sulphate fibre with about 10% birch sulphate. The brightness was 84% SCAN and the beating degree was 27° SR.

Pulp mixtures, which were dried and tested as in Example 4, were made from this pulp and mechanical wood pulp according to Example 4.

| Results: | 25% mechanical wood pulp | 60% mechanical wood pulp | 95% mechanical wood pulp |
|---|---|---|---|
| Proportion of non-defibrate % | 7 | 6 | 7 |
| Bulk, cm³/g | 24.2 | 21.1 | 19.0 |
| Time for complete wetting, minutes | 1.2 | 1.6 | 1.8 |
| Liquid retention capacity, grams water/grams pulp | 7.3 | 6.8 | 6.6 |
| Liquid spreading capacity, grams water/grams pulp × minutes | 6.08 | 4.25 | 3.66 |
| Bursting strength, Newton | 0.51 | 0.36 | 0.24 |
| Impact loss % | 4 | 8 | 12 |

EXAMPLE 8

Waste paper, mainly newspaper, was slurried in water at about 45° C containing 3% by weight waterglass and 2% by weight sodium peroxide, based on the weight of the paper. After the paper was considered well slurried, 3% by weight of soft soap was added based on the weight of the paper, whereupon the slurry was allowed to stand under slow stirring for 90 minutes. The pulp concentration was about 0.5%.

Thereafter, printing ink was removed by flotation as in Example 7.

A flash-dried sample of the pulp was analyzed and found to consist mainly of mechanical wood pulp fibres with about 20% chemical pulp fibre from pine or fir.

Pulp mixtures, which were dried and examined as in Example 4, were made from this pulp and paper pulp according to Example 3.

| Results: fibre | 25% recycled fibre | 60% recycled fibre | 95% recycled fibre |
|---|---|---|---|
| Proportion of non-defibrate % | 7 | 6 | 7 |
| Bulk, cm³/g | 22.0 | 21.0 | 20.7 |
| Time for complete wetting minutes | 1.6 | 1.9 | 2.2 |
| Liquid retention capacity, grams water/grams pulp | 6.6 | 6.6 | 6.5 |
| Liquid spreading capacity, grams water/grams pulp × minutes | 4.13 | 3.47 | 2.96 |
| Bursting strength, Newton | 0.25 | 0.23 | 0.21 |
| Impact loss % | 5 | 11 | 16 |

The invention is not limited to the working examples described above, but can be modified in a number of ways. The mechanical wood pulp can thus be produced according to several different methods such as the stone grinder method, the disc refiner method or a thermomechanical method, and from several kinds of wood having different freeness, and may be treated with different bleaching and surface active agents. Furthermore, the recycled pulp fibre can be produced from different qualities of waste paper, bleached, unbleached or coloured, woodfree or wood-containing, or from mixed waste paper, and by means of a plurality of different deblackening, cleaning and bleaching methods. The chemical pulp included can also be produced in different ways such as the sulphite method, the sulphate method, the magnetite method, etc. or from different woods with long or short fibres, and can have different refining degrees and different brightness.

What we claim is:

1. A method of producing fluffed pulp for use in products for absorbing liquids, characterized in that an aqueous slurry of chemical pulp is beaten so that its drainage resistance exceeds 20° SR, 95–25% by weight mechanical wood pulp and 5–75% by weight of said chemical pulp beaten in a wet state are mixed with each other, and then the total pulp is dewatered mechanically to a dry solids content of 40–50% by weight, coarse-defibrated, dried in a flash drying step to 60–85% by weight, finish-defibrated and finish-dried to 80–95% by weight dry solids content.

2. A method of producing fluffed pulp as claimed in claim 1, characterized in that the total pulp consists of more than 25% by weight of waste fibres which have been produced by de-inking paper scrap.

3. A method of producing fluffed pulp as claimed in claim 2, characterized in that the de-inked paper scrap is bleached.

4. A fluffed pulp produced according to the method of claim 1, for use in products for absorbing liquids, characterized in that it has a liquid retention capacity of at least 6.5 g liquid per gram pulp, a liquid dispersion capacity of at least 2.5 g liquid per gram pulp per minute, a bulk of at least 18 cm³ per gram and a web strength of at least 0.2 Newton.

* * * * *